US012575902B2

(12) United States Patent
Xiao et al.

(10) Patent No.: US 12,575,902 B2
(45) Date of Patent: Mar. 17, 2026

(54) ADAPTER AND SURGICAL ASSISTANCE SYSTEM

(71) Applicant: ROBGENIX MEDICAL PTE. LTD., Singapore (SG)

(72) Inventors: Sa Xiao, Shanghai (CN); Hao Chen, Shanghai (CN); Cunwang Ge, Shanghai (CN); Gang Wu, Shanghai (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/056,120

(22) Filed: Feb. 18, 2025

(65) Prior Publication Data

US 2026/0047903 A1 Feb. 19, 2026

Related U.S. Application Data

(63) Continuation of application No. PCT/CN2024/140576, filed on Dec. 19, 2024.

(30) Foreign Application Priority Data

Aug. 15, 2024 (CN) .......................... 202411126095.1

(51) Int. Cl.
A61B 34/35 (2016.01)
A61B 17/00 (2006.01)
A61B 34/30 (2016.01)

(52) U.S. Cl.
CPC .............. *A61B 34/35* (2016.02); *A61B 17/00* (2013.01); *A61B 2017/00398* (2013.01);
(Continued)

(58) Field of Classification Search
CPC ................... A61B 34/35; A61B 17/00; A61B 2017/00398; A61B 2017/00486;
(Continued)

(56) References Cited

U.S. PATENT DOCUMENTS

2011/0288573 A1* 11/2011 Yates ..................... A61B 50/36
227/175.1

FOREIGN PATENT DOCUMENTS

CN 106535783 A * 3/2017 ........... A61B 17/068
CN 109199494 A 1/2019
(Continued)

OTHER PUBLICATIONS

English translation of CN 106535783 (Year: 2017).*
(Continued)

*Primary Examiner* — Carrie R Dorna
*Assistant Examiner* — Joshua Daryl D Lannu
(74) *Attorney, Agent, or Firm* — Nixon & Vanderhye P.C.

(57) ABSTRACT

The present disclosure provides an adapter and a surgical assistance system, where the adapter includes an instrument driving device and an installation platform, the instrument driving device is provided on the installation platform, the adapter is installed on a surgery performing device via the installation platform, a motor in the surgery performing device is configured to drive the instrument driving device, and the instrument driving device is configured to drive the surgical instrument; the installation platform includes a counting rack, a platform body and an installation bottom plate, where the platform body is in transmission connection with a power output shaft of the surgery performing device via the installation bottom plate, and the counting rack is installed on the platform body and configured to limit the usage times of the adapter. The adapter provided by the present disclosure can limit the usage times of the adapter by the counting rack, thereby preventing it from being reused after exceeding the set effective usage times, and avoiding the occurrence of unexpected failures of the adapter beyond its lifespan.

12 Claims, 13 Drawing Sheets

100

210 220

200

(52) U.S. Cl.
CPC .............. *A61B 2017/00486* (2013.01); *A61B 2017/00725* (2013.01); *A61B 2034/301* (2016.02); *A61B 2034/304* (2016.02)

(58) Field of Classification Search
CPC .... A61B 2017/00725; A61B 2034/301; A61B 2034/304
See application file for complete search history.

(56)                    References Cited

FOREIGN PATENT DOCUMENTS

| CN | 115590598 A | * | 1/2023 | ....... A61B 17/00234 |
|----|-------------|---|--------|-----------------------|
| CN | 115835829 A |   | 3/2023 | |
| CN | 118217016 A |   | 6/2024 | |
| GB | 816938 A    |   | 7/1959 | |
| WO | WO 2015/088142 A1 | | 6/2015 | |

OTHER PUBLICATIONS

English Translation of CN115590598 (Year: 2023).*
Written Opinion and Search Report mailed Apr. 24, 2025 in International Application No. PCT/CN2024/140576, with English translation, 18 pages.

* cited by examiner

310

312

312a

311

220        231        221        230        210

212

211

220

221

210

220

221

210

剩余使用次数

10/13

ADAPTER AND SURGICAL ASSISTANCE SYSTEM

CROSS-REFERENCE TO RELATED APPLICATIONS

This application is a continuation of International Application No. PCT/CN2024/140576 filed Dec. 19, 2024, which designated the U.S. and claims priority to Chinese Patent Application No. 202411126095.1 filed Aug. 15, 2024, the entire contents of each of which are hereby incorporated by reference.

TECHNICAL FIELD

The present disclosure relates to the technical field of medical devices, and particularly to an adapter and a surgical assistance system.

BACKGROUND

Currently, mitral regurgitation is typically treated by minimally invasive surgery. In particular, a valve repair device is delivered to a mitral valve of a patient by a catheter system and is operated remotely in vitro to repair the diseased mitral valve, thereby treating the mitral regurgitation. The catheter system is of a multi-layered structure, which has an outer sheath configured to penetrate the right atrium through a femoral vein and then pass through an interatrial septum to enter the left atrium so as to deliver the valve repair device to the mitral valve.

The use of the catheter system requires manual operations by a doctor, which are difficult and highly demanding in terms of technical skill and clinical experience, thereby causing a long learning curve for doctors and to some extent restricting the development of the surgical procedure or the clinical use of the devices. Moreover, during the surgical procedure, doctors mostly need to perform the surgery under the cooperation of CT (Computed Tomography) equipment, resulting in prolonged exposure of medical staff to a radiative environment, which can cause certain harm to the health of the medical staff. Therefore, it is necessary to provide a catheter adapter by which the catheter system can be remotely operated to improve the working environment for the medical staff and shorten the learning curve for doctors.

SUMMARY

As for the above problems in the prior art, an adapter and a surgical assistance system are provided, by which a catheter system can be remotely operated, a working environment of the medical staff can be improved and a learning curve of doctors can be shortened.

The present disclosure provides the following solutions.

In a first aspect, the present disclosure provides an adapter including an installation platform and an instrument driving device provided on the installation platform, the installation platform being installed on a surgery performing device; where the instrument driving device is in transmission connection with the surgery performing device and is configured to drive a surgical instrument; and the installation platform includes a counting rack, a platform body and an installation bottom plate, where the platform body is in transmission connection with a power output shaft of the surgery performing device via the installation bottom plate, and the counting rack is installed on the platform body and configured to limit the usage times of the adapter.

In some possible embodiments, the adapter provided herein further includes: a transmission shaft;

one end of the transmission shaft is in transmission connection with the power output shaft, and the other end of the transmission shaft is in transmission connection with the instrument driving device;

the transmission shaft is provided with locking tabs, the counting rack is provided in a horizontal plane in a preset direction, a first row of teeth is provided on a side of the counting rack adjacent to the transmission shaft, and the preset direction comprises an axial direction of the transmission shaft; and the locking tabs are configured to extend into a groove of the first row of teeth and push an edge of the groove when the transmission shaft rotates, so that the counting rack is moved by a first distance in the preset direction.

In some possible embodiments, the locking tab each includes a ring body and a locking tab protrusion;

a ring width of the ring body in a radial direction is less than or equal to a distance between the transmission shaft and a tooth crest of the counting rack;

a length of the locking tab protrusion in the radial direction is greater than the distance between the transmission shaft and the tooth crest of the counting rack and less than or equal to the distance between the transmission shaft and the groove of the counting rack;

the locking tab protrusion is provided with a first ramp of a preset height in an axial direction, and when the transmission shaft rotates, the first ramp pushes the edge of the groove, so that the counting rack is moved by a first distance in the preset direction.

In some possible embodiments, the installation bottom plate comprises a bottom plate protrusion and the platform body is provided with a second ramp;

the counting rack is provided with a second row of teeth at a side opposite to the first row of teeth, the first row of teeth and the second row of teeth are disposed alternately, and the second ramp is disposed below the second row of teeth;

the bottom plate protrusion is used to lift the counting rack to separate the counting rack from the second ramp when the adapter is installed on the surgery performing device;

when the adapter is detached from the surgery performing device, the installation bottom plate is separated from the platform body, and an edge of one of the grooves of the second row of teeth of the counting rack slides down along the second ramp, so that the counting rack is moved by a second distance in the preset direction.

In some possible embodiments, the platform body further includes a compression spring;

an upper end of the compression spring is connected to the platform body, and a lower end of the compression spring abuts against the counting rack;

when the adapter is detached from the surgery performing device, the installation bottom plate is separated from the platform body, the compression spring presses down the counting rack, and the edge of the groove of the second row of teeth of the counting rack slides down along the second ramp, so that the counting rack is moved by a second distance in the preset direction.

In some possible embodiments, the counting rack is provided with a counting scale, the platform body is provided with a pointing mark, and the counting scale pointed by the pointing mark indicates the remaining usage times of the adapter;

the distance between every two counting scales is the sum of the first distance and the second distance.

In some possible embodiments, when the remaining usage times of the adapter is 0, an end of the first row of teeth of the counting rack is stuck with the locking tab, so that the transmission shaft is non-rotatable.

In some possible embodiments, a push-pull drive assembly is further included;

the push-pull drive assembly includes a reel device and a flexible push-pull wire provided between the instrument driving device and the reel device, and a reel shaft of the reel device is in transmission connection with the power output shaft of the surgery performing device.

In some possible embodiments, the reel device includes a first reel and a second reel that are coaxial;

one end of the flexible push-pull wire is connected to the second reel, and the other end of the flexible push-pull wire is connected to the first reel by passing through the instrument driving device;

the first reel and the second reel are configured to be twisted to tighten the flexible push-pull wire.

In some possible embodiments, the first reel includes a transmission disc and a reel body;

the reel shaft is a D-shaped reel shaft, and the transmission disc comprises a central through hole matching the shape of the reel shaft and a screw slot including a plurality of slot positions;

the reel body is provided with a fixed hole configured to be is fixed relative to one of the slot positions of the screw slot via the screw;

the plurality of slot positions in the screw slot are used for adjusting a relative angle between the reel body and the transmission disc to tighten the flexible push-pull wire.

In some possible embodiments, the reel shaft of the reel device is in transmission connection with the power output shaft of the surgery performing device via a magnetic torque coupling.

In some possible embodiments, the instrument driving device is provided with a plurality of pins;

the plurality of pins are configured for adapting to a variety of surgical instruments.

In a second aspect, the present disclosure provides a surgical assistance system including a surgery performing device and the adapter, wherein the surgery performing device is configured to drive the adapter.

For the adapter and the surgical assistance system provided by the embodiments of the present disclosure, a surgical instrument can be remotely driven by an instrument driving device, so that medical staff can avoid long-term exposure to radiation, thereby improving the working environment of medical staff and shortening the learning curve of a doctor. In addition, the adapter in the present disclosure can limit the usage times of the adapter by the counting rack, thereby preventing it from being reused after exceeding the set effective number of uses, and avoiding the occurrence of unexpected failures of the adapter beyond its lifespan.

Other advantages of the present disclosure will be explained in more detail in conjunction with the following description and the accompanying drawings.

It should be understood that the above description is only an overview of the technical solutions of the present disclosure, so that the technical means of the present disclosure can be more clearly understood, and thus can be implemented according to the description. In order that the above and other objectives, features, and advantages of the present disclosure may be more readily understood, the following detailed description of the present disclosure is set forth.

BRIEF DESCRIPTION OF THE DRAWINGS

Advantages and benefits described herein, as well as other advantages and benefits, will become apparent to a person skilled in the art upon reading the following detailed description of exemplary embodiments. The drawings are only for purposes of illustrating exemplary embodiments and are not to be construed as limiting the present disclosure. In the drawings.

Figure 1:
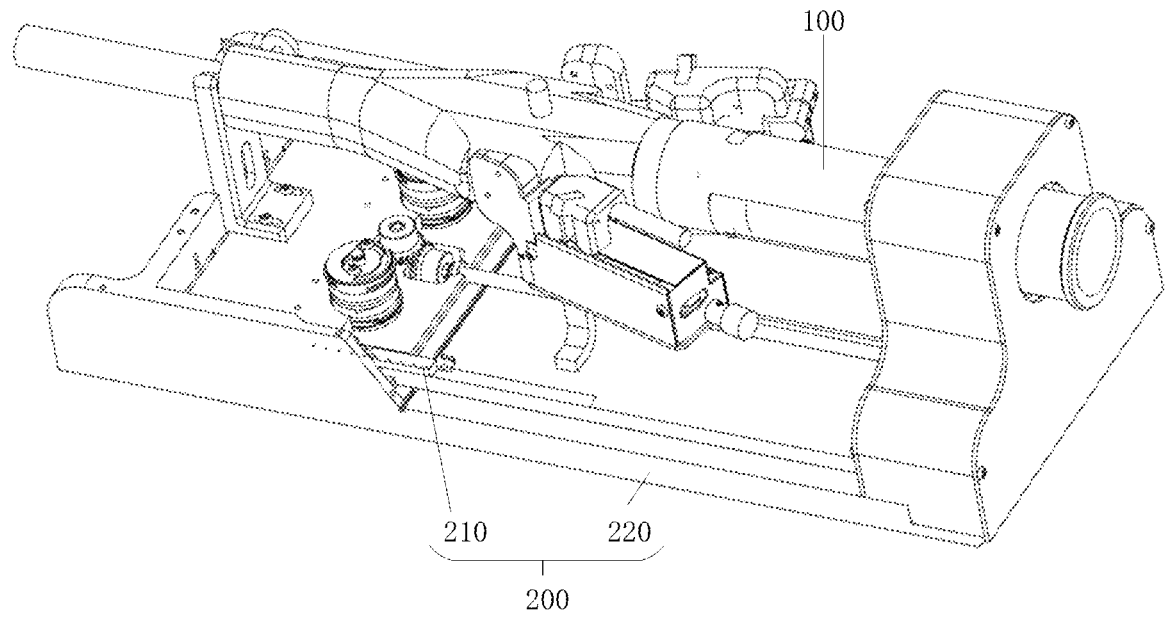
FIG. 1 is a schematic diagram illustrating an adapter according to an embodiment of the present disclosure.

In the drawings, the components identified by the reference numerals are listed as follows:

instrument driving device 100; installation platform 200; counting rack 210; first row of teeth 211; second row of teeth 212; platform body 220; second ramp 221; compression spring 222; pointing mark 223; transmission shaft 300; locking tab 310; ring body 311; locking tab protrusion 312; first ramp 312a; reel device 400; reel shaft 410; magnetic torque coupling 411; first reel 420; transmission disc 421; central through hole 421a; screw slot 421b; first screw slot 421bl; second screw slot 421b2; reel body 422; fixed hole 422a; first fixed hole 422al; second fixed hole 422a2; reel central hole 422b; screw 423; second reel 430; flexible push-pull wire 500; sheath 501; steering wheel 502; first pin 610; second pin 620; third pin 630; surgical instrument 700.

In the drawings, the same or corresponding reference numerals indicate the same or corresponding parts.

DETAILED DESCRIPTION

Exemplary embodiments of the present disclosure will be described in more detail below referring to the accompanying drawings. Although the exemplary embodiments of the present disclosure are shown in the drawings, it should be understood that the present disclosure can be implemented in various forms and should not be limited to the embodiments described herein. Rather, these embodiments are provided so that the present disclosure will be understood more thoroughly, and will fully convey the scope of the present disclosure to a person skilled in the art.

In the description of the embodiments of the present disclosure, it should be understood that terms such as "including" or "having" are intended to indicate the presence of the disclosed features, numerals, steps, actions, components, parts, or combinations thereof in the specification, and do not exclude the possibility of the presence of one or more other features, numerals, steps, actions, components, parts, or combinations thereof. The terms "first", "second" and the like are used for distinguishing between similar or identical features for convenience of description only and are not to be construed as indicating or implying a relative importance or number of such features. Thus, a feature defined by "first", "second", etc. may explicitly or implicitly include one or more of such features. In the description of the embodiments of the present disclosure, unless otherwise specified, the term "a plurality of" means two or more than two.

"/" means, unless otherwise stated, for example, A/B may represent A or B; as used herein, "and/or" is merely an association relationship describing an associated object, meaning that there may be three relationships, e.g., A and/or B, which may mean: there are three cases of A alone, A and B together, and B alone. For ease of description, spatial relationship terms such as "below", "under", "above", "on", and the like may be used herein to describe one element or feature's relationship to other elements or features illustrated in the figures. It will be understood that the spatial relationship terms are intended to encompass other orientations of the device in use or operation in addition to the orientation depicted in the accompanying drawings.

In addition, it should be noted that the embodiments and features of the embodiments in the present disclosure can be combined with each other without conflict. The present disclosure will now be described in detail in connection with the embodiments referring to the accompanying drawings.

Referring to FIG. 1, FIG. 1 is a schematic diagram illustrating an adapter according to an embodiment of the present disclosure.

As shown in FIG. 1, the adapter according to an embodiment of the present disclosure includes an instrument driving device apparatus 100 and an installation platform 200;

the instrument driving device 100 is provided on the installation platform 200, where an adapter is installed on a surgery performing device via the installation platform 200, a motor in the surgery performing device is configured to drive the instrument driving device 100, and the instrument driving device 100 is configured to drive the surgical instrument;

the installation platform 200 includes a counting rack 210, a platform body 220 and an installation bottom plate (not shown in the figures), where the platform body 220 is in transmission connection with a power output shaft of the surgery performing device via the installation bottom plate, the counting rack 210 is installed on the platform body 220, and the counting rack 210 is configured to limit the usage times of the adapter.

It can be seen therefrom that for the adapter and the surgical assistance system provided by the embodiment of the present disclosure, a surgical instrument can be remotely driven by an instrument driving device, so that medical staff can avoid long-term exposure to radiation, thereby improving the working environment of medical staff and shortening the learning curve of a doctor. In addition, the adapter in the present disclosure can limit the usage times of the adapter by the counting rack, thereby preventing it from being reused after exceeding the set effective usage times, and avoiding the occurrence of unexpected failures of the adapter beyond its lifespan.

Figure 2:
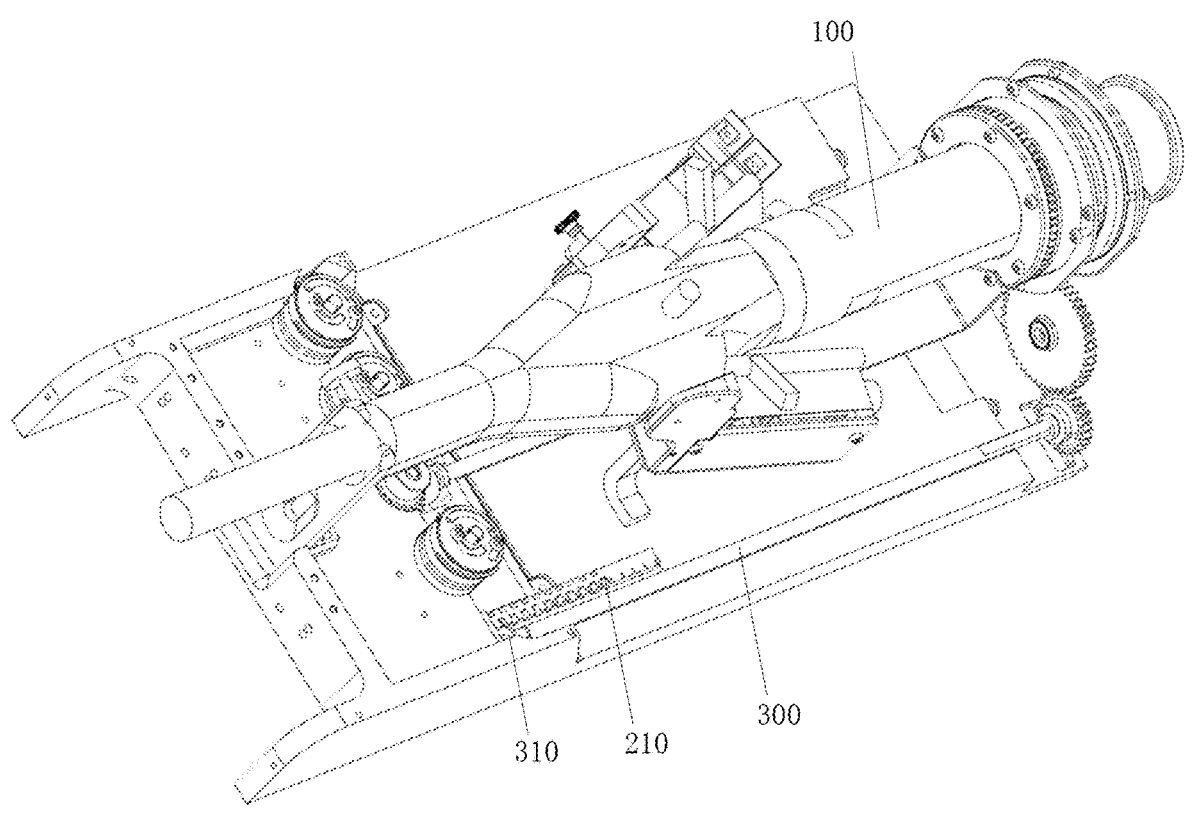
FIG. 2 is a schematic diagram illustrating another adapter according to an embodiment of the present disclosure.
Figure 3:
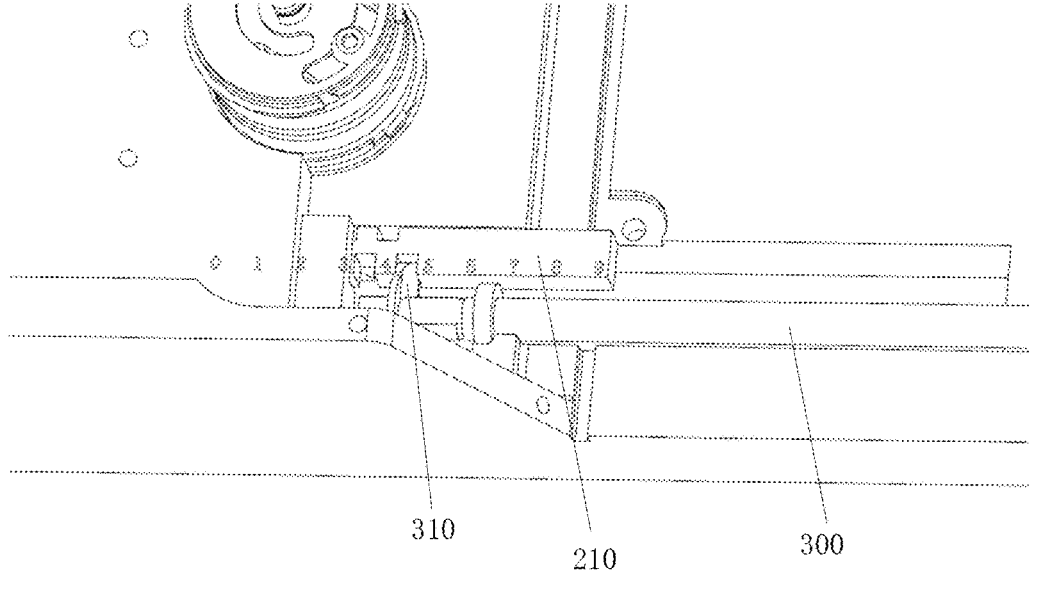
FIG. 3 is a schematic diagram illustrating a counting rack and its associated components according to an embodiment of the present disclosure.

As shown in FIGS. 2 and 3, the adapter provided by the embodiment of the present disclosure further includes: a transmission shaft 300. One end of the transmission shaft 300 is in transmission connection with the power output shaft of the surgery performing device, and the other end of the transmission shaft 300 is in transmission connection with the instrument driving device 100; the transmission shaft 300 is provided with locking tabs 310, and the counting rack 210 is provided in a horizontal plane in a preset direction. It should be noted that the preset direction includes the axial direction of the transmission shaft, and in practice, the preset direction may also be other directions, such as the radial direction of the transmission shaft, which is not limited by the embodiment of the present disclosure. A side of the counting rack 210 adjacent to the transmission shaft 300 is provided with a first row of teeth; when the transmission shaft 300 rotates, the locking tabs 310 are configured to extend into the grooves of the first row of teeth and push an edge of the groove, so that the counting rack 210 moves a first distance in the preset direction.

Figure 4:
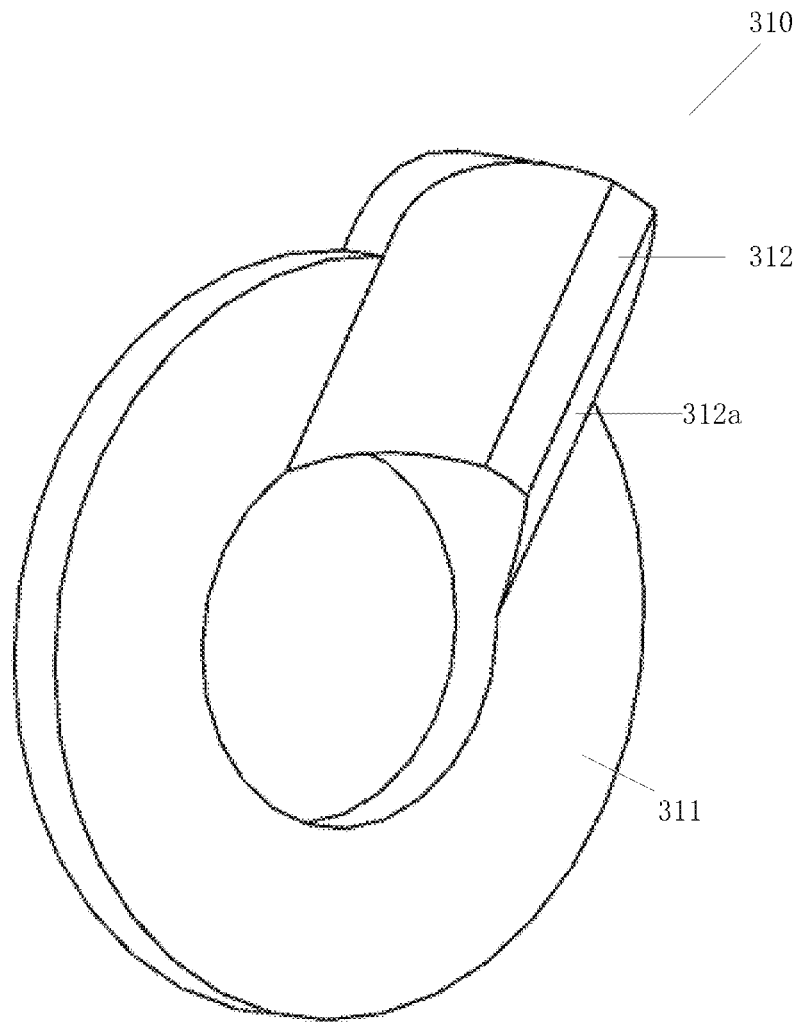
FIG. 4 is a schematic diagram illustrating a locking tab according to an embodiment of the present disclosure.

As shown in FIG. 4, the locking tab 310 includes a ring body 311 and a locking tab protrusion 312; a ring width of the ring body 311 in the radial direction is less than or equal to the distance between the transmission shaft 300 and the tooth crest of the counting rack 210; the length of the locking tab protrusion 312 in the radial direction is greater than the distance between the transmission shaft 300 and the tooth crest of the counting rack 210, and is less than or equal to the distance between the transmission shaft 300 and the groove of the counting rack 210; the locking tab protrusion 312 is provided with a first ramp 312a of a preset height in an axial direction, and when the transmission shaft 300 rotates, the first ramp 312a pushes the edge of the groove, so that the counting rack 210 moves a first distance in the preset direction. It should be noted that the first distance in the embodiment of the present disclosure is positively correlated with the height of the first ramp 312a in the axial direction. In general, the first distance may be equal to the height of the first ramp 312a in the axial direction.

Figure 5:
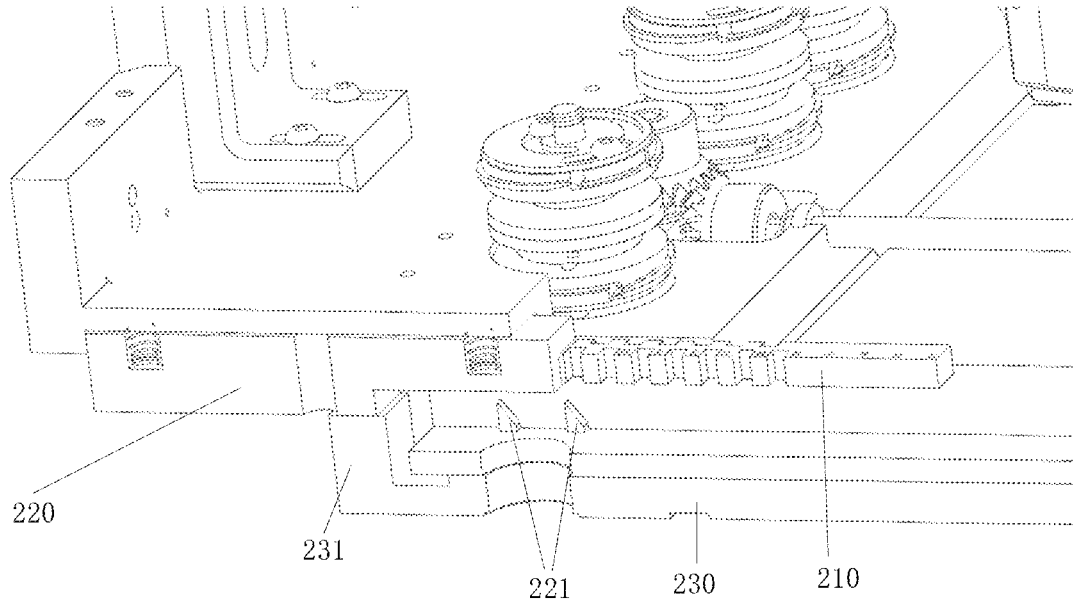
FIG. 5 is a schematic diagram illustrating an installation bottom plate and a platform body according to an embodiment of the present disclosure.
Figure 6:
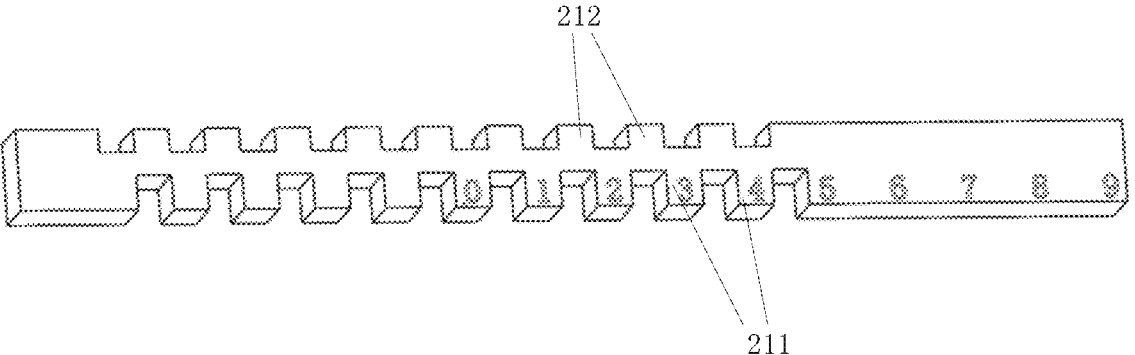
FIG. 6 is a schematic diagram illustrating a counting rack according to an embodiment of the present disclosure.
Figure 7:
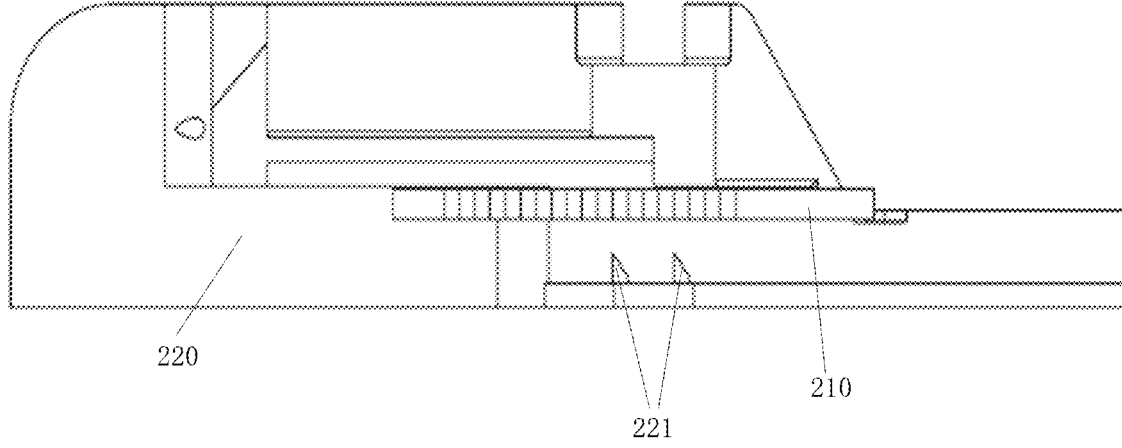
FIG. 7 is a schematic diagram illustrating an installation bottom plate and a platform body according to an embodiment of the present disclosure.

As shown in FIG. 5, the installation bottom plate 230 provided in the embodiment of the present disclosure includes a bottom plate protrusion 231, and the platform body 220 is provided with a second ramp 221. As shown in FIG. 6, the counting rack 210 is provided with a second row of teeth 212 at a side opposite to the first row of teeth 211, the first row of teeth 211 and the second row of teeth 212 are disposed alternately, and the second ramp 221 is disposed below the second row of teeth 212. As shown in FIGS. 5 and 7, the bottom plate protrusion 231 is used to lift the counting rack 210 to cause the counting rack 210 to separate from the second ramp 221 when the adapter is installed on the surgery performing device.

Figure 8:
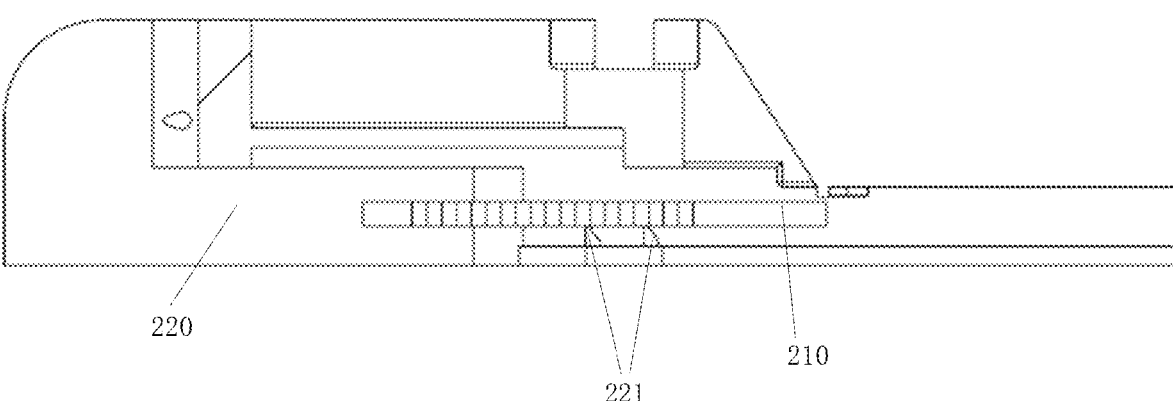
FIG. 8 is a schematic diagram illustrating another installation bottom plate and a platform body according to an embodiment of the present disclosure.

As shown in FIG. 8, when the adapter is detached from the surgery performing device, the installation bottom plate 230 is separated from the platform body 220, and an edge of one of the grooves of the second row of teeth 212 of the counting rack 210 slides down along the second ramp 221, so that the counting rack 210 moves a second distance in the preset direction. It should be noted that when the adapter is detached from the surgery performing device, the adapter has been used once, so that the counting rack 210 has been moved a first distance in a preset direction under the push of the locking tab, at this time, the edge of one groove of the second row of teeth 212 of the counting rack 210 will move to an upper part of the second ramp 221. When the installation bottom plate 230 is separated from the platform body 220, the bottom plate protrusion 231 no longer lifts the counting rack 210, the counting rack 210 falls down, and the edge of one groove of the second row of teeth 212 of the counting rack 210 will slide down along the second ramp 221, causing the counting rack 210 to move a second distance in the preset direction. The second distance in the embodiment of the present disclosure is related to the length of the second ramp 221 in the preset direction, and in general, the second distance may be equal to or less than the length of the second ramp 221 in the preset direction.

Figure 9:
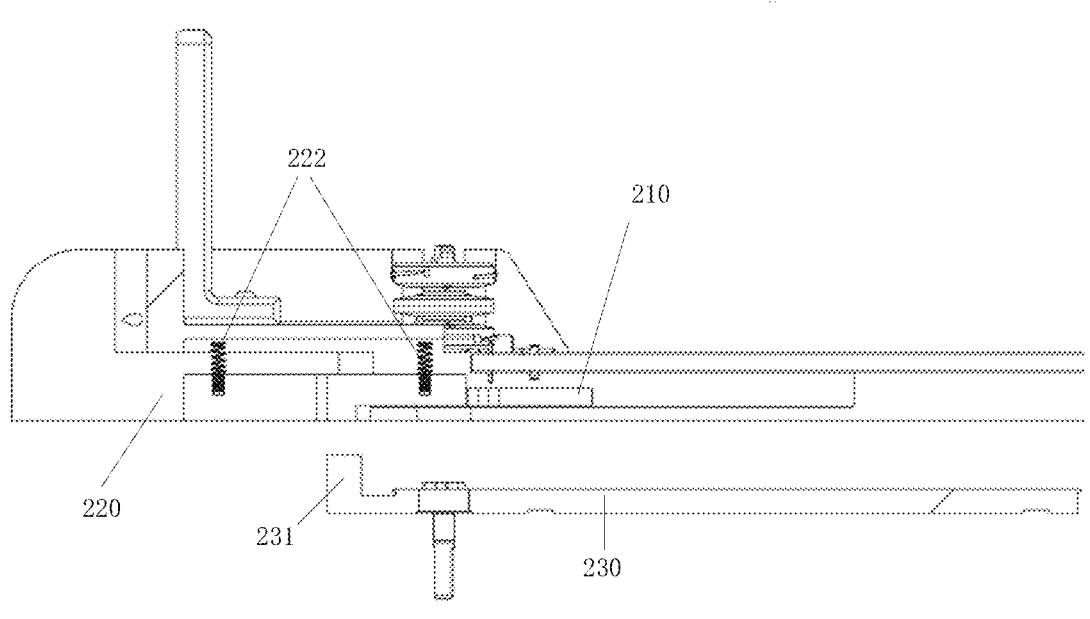
FIG. 9 is a schematic diagram illustrating an installation bottom plate and a platform body according to an embodiment of the present disclosure.

In some possible embodiments, the embodiment of the present disclosure may also provide a compression spring on the platform body 220, when the adapter is detached from the surgery performing device, the compression spring causes an edge of a groove of the second row of teeth 212 of the counting rack 210 to slide down along the second ramp 221. As shown in FIG. 9, the platform body 220 also includes a compression spring 222. An upper end of the compression spring 222 is connected to the platform body 220, and a lower end of the compression spring 222 abuts against the counting rack 210. When the adapter is detached from the surgery performing device, the installation bottom plate 230 is separated from the platform body 220, the compression spring 222 presses down the counting rack 210, and the edge of the groove of the second row of teeth 212 of the counting rack 210 slides down along the second ramp 221, so that the counting rack 210 moves a second distance in the preset direction.

Figure 10:
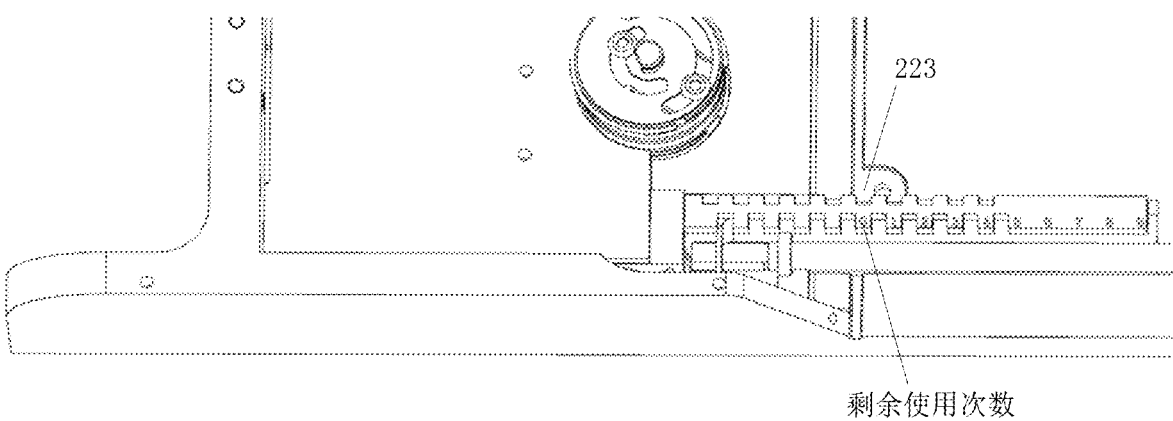
FIG. 10 is a schematic diagram illustrating a counting rack and its associated components according to an embodiment of the present disclosure.

In some possible embodiments, the counting rack 210 in the embodiment of the present disclosure may also indicate the remaining usage times of the adapter, facilitating users to plan the usage times of the adapter, and replacing the adapter in a timely manner after the usage times are completely used up. As shown in FIG. 6, the counting rack 210 may be provided with a counting scale. As can be seen from the above, during one installation, usage and disassembly process of the adapter, the counting rack 210 moves a total distance equal to the sum of the first distance and the second distance in the preset direction. Thus, the distance between every two counting scales on the counting rack may be the sum of the first distance and the second distance. In this way, every time the adapter is used once, the counting rack is moved by one counting scale. As shown in FIG. 10, the platform body 220 is provided with a pointing marker 223, and the counting scale pointed by the pointing marker 223 indicates the remaining usage times of the adapter.

Figure 11:
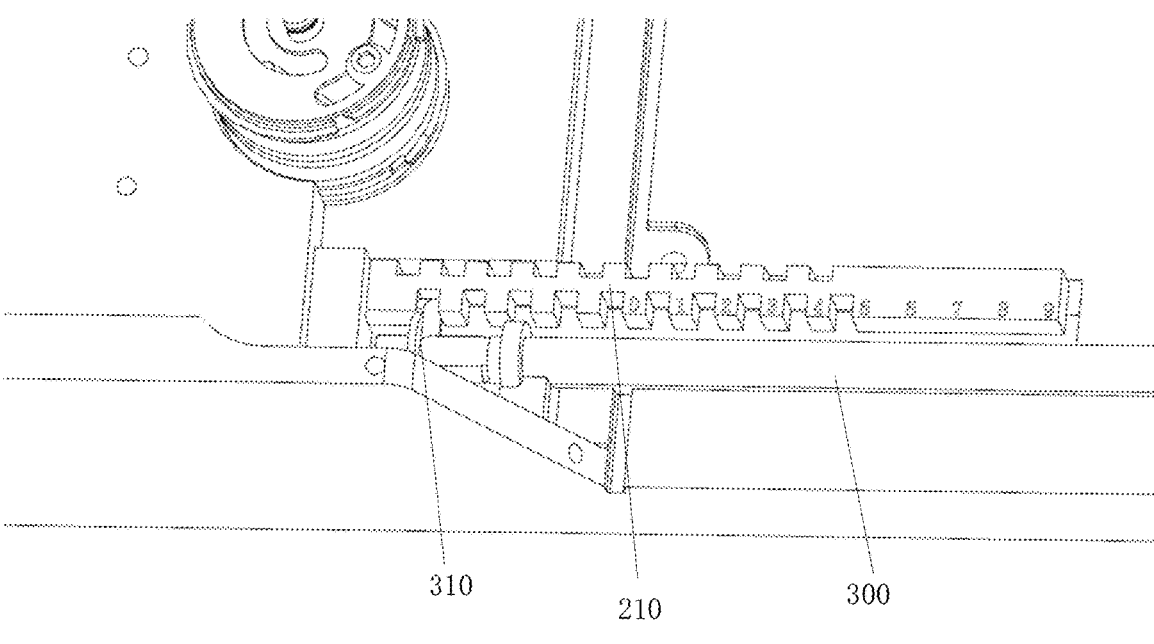
FIG. 11 is a schematic diagram illustrating another relationship between a counting rack and a locking tab according to an embodiment of the present disclosure.

To prevent the adapter from being reused after exceeding the set effective usage times and to avoid the occurrence of unexpected failures of the adapter beyond its lifespan, in the present disclosure, a corresponding locking device can be provided when the remaining usage times of the adapter is 0. As shown in FIG. 11, when the adapter is used for the last time, the locking tab 310 moves to the last groove of the first row of teeth 211, and when the adapter is detached from the surgery performing device, under the action of the second ramp 221, the counting rack 210 moves a second distance in a preset direction, at this time, the locking tab has moved to the rear of the last groove of the first row of teeth 211, that is, the end of the first row of teeth 211, where no groove is provided. Since the length of the locking tab protrusion 312 of the locking tab 310 in the radial direction is greater than the distance between the transmission shaft 300 and the tooth crest of the counting rack 210, the locking tab protrusion 312 of the locking tab 310 abuts against the end of the first row of teeth 211, that is, the locking tab 310 is stuck with the end of the first row of teeth 211 in the counting rack 210, so that the transmission shaft 300 cannot be rotated, and thus preventing the adapter from being reused.

In summary, the adapter in the present disclosure can cooperate with the first ramp of the locking tab on the transmission shaft and the second ramp on the platform body via the counting rack, so that each time the adapter is used, the counting rack is moved by one counting grid, and after the counting rack is moved to the last counting grid, the locking tabs on the transmission shaft and the counting slip are stuck with each other, so that the transmission shaft cannot rotate and the adapter cannot be reused. As such, the adapters provided by the embodiment of the present disclosure may limit the usage times thereof, thereby preventing it from being reused after exceeding the set effective usage times, and avoiding the occurrence of unexpected failures of the adapter beyond its lifespan.

In addition, the adapter provided by the embodiment of the present disclosure may also include a push-pull drive assembly.

Figure 12:
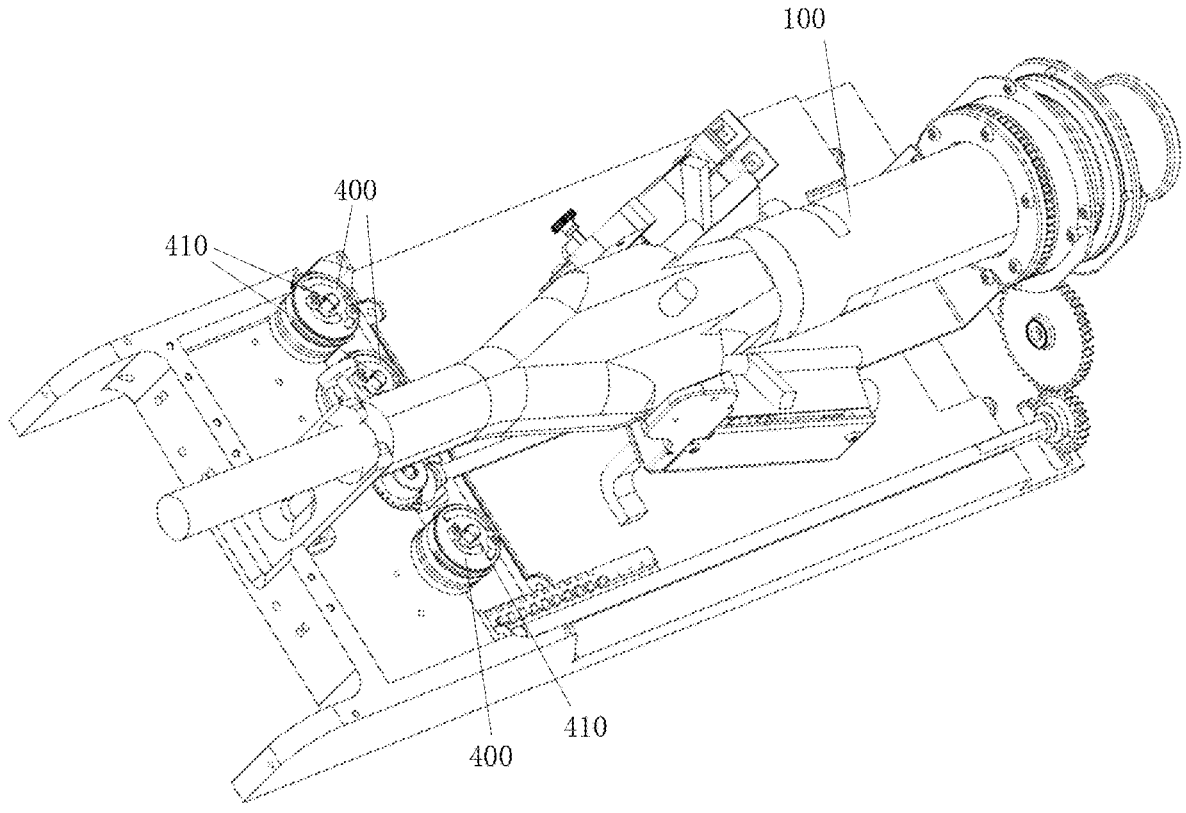
FIG. 12 is a schematic diagram illustrating an adapter according to an embodiment of the present disclosure.

As shown in FIG. 12, the push-pull drive assembly includes a reel device 400 and a flexible push-pull wire (not shown in the figure), where the flexible push-pull wire is disposed between the instrument driving device 100 and the reel device 400, and a reel shaft 410 of the reel device 400 is in transmission connection with the power output shaft of the surgery performing device. It should be noted that the reel device 400 and the flexible push-pull wire convert the motion of the driving member such as a motor into the displacement motion of the instrument driving device 100, thereby simplifying the motion transmission chain, enabling the instrument driving device to be lightweight and miniaturized, and reducing the processing cost.

Figure 13:
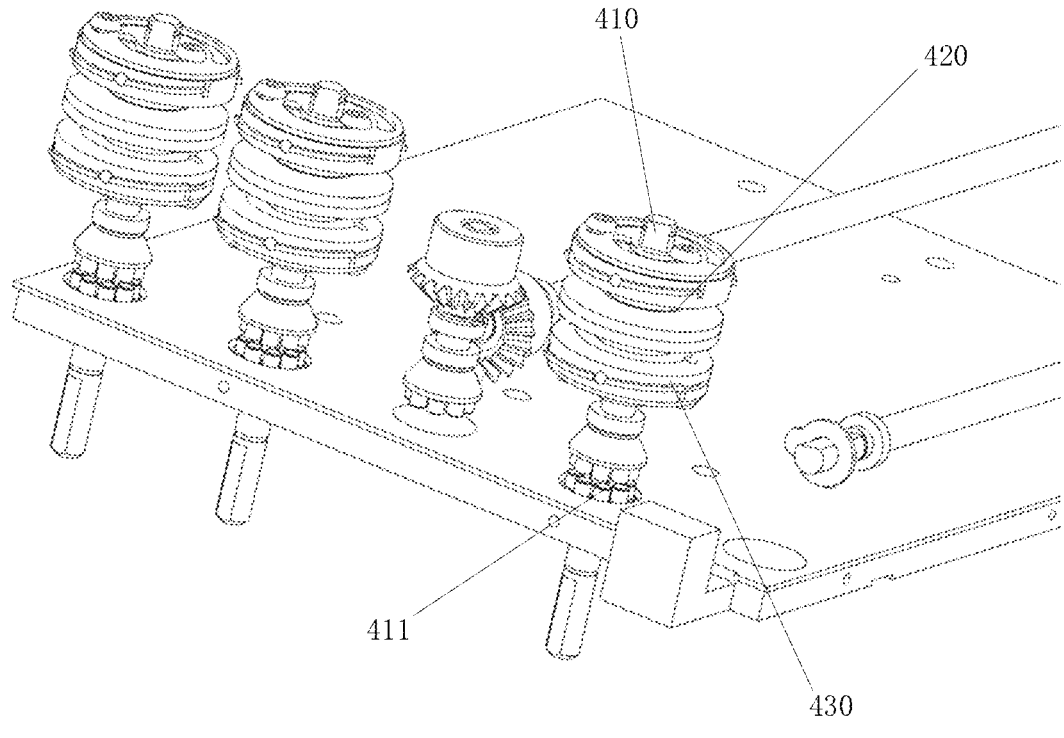
FIG. 13 is a schematic diagram illustrating a reel device and its associated components according to an embodiment of the present disclosure.

As shown in FIG. 13, the reel device 400 provided by the embodiments of the present disclosure may include a first reel 420 and a second reel 430 that are coaxial. One end of the flexible push-pull wire is connected to the second reel 430, and the other end of the flexible push-pull wire is connected to the first reel 420 by passing through the instrument driving device 100; the first reel 420 and the second reel 430 may be twisted to tighten the flexible push-pull wire. As a possible implementation, the reel shaft 410 of the reel device 400 in the embodiment of the present disclosure may be in transmission connection with the power output shaft of the surgery performing device via a magnetic torque coupling 411. The reel shaft 410 of the reel device 400 may be in transmission connection with the power output shaft of the surgery performing device via the magnetic torque coupling 411, according to the embodiment of the present disclosure, the surgical equipment may be protected from accidental damage during use by utilizing the overload slipping characteristics of the magnetic torque coupling 411.

Figure 14:
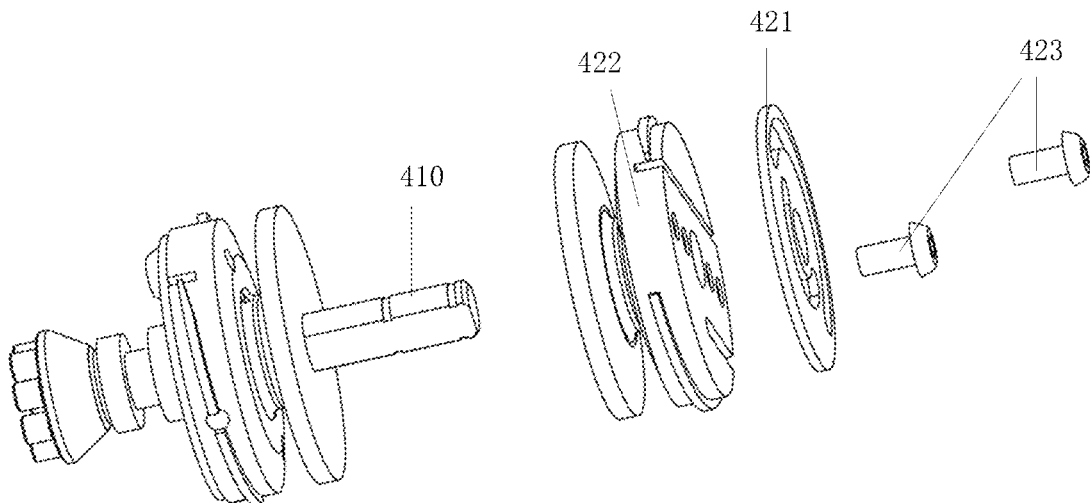
FIG. 14 is a schematic diagram illustrating a reel device according to an embodiment of the present disclosure.
Figure 15:
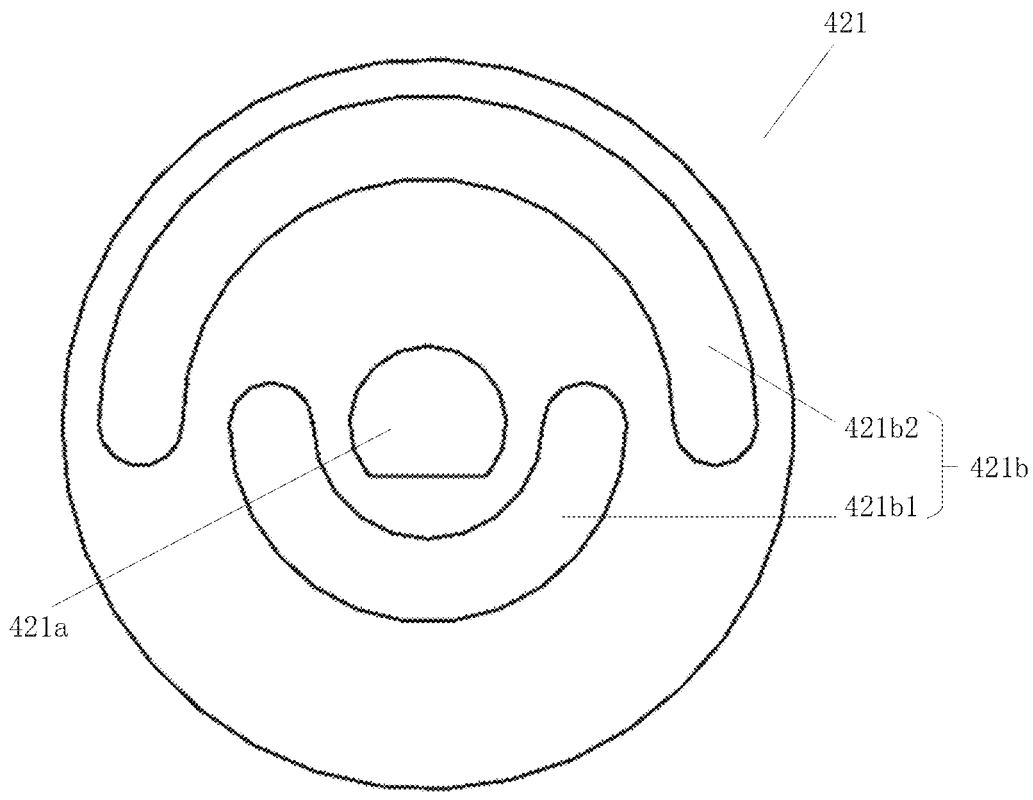
FIG. 15 is a schematic diagram illustrating a transmission disc according to an embodiment of the present disclosure.

As shown in FIG. 14, the first reel 420 includes a transmission disc 421, a reel body 422, and a screw 423. As shown in FIG. 15, the reel shaft 410 is a D-shaped reel shaft, and the transmission disc includes a central through hole 421*a* and a screw slot 421*b*, and the central through hole 421*a* matches the shape of the reel shaft 410. When the reel shaft 410 rotates, the rotation of the transmission disc 421 is caused through the central through hole 421*a*. The screw slot 421*b* includes a plurality of slot positions. It should be noted that the screw slot 421*b* in FIG. 15 specifically includes a first screw slot 421*b*1 and a second screw slot 421*b*2 which are independent from each other, and each of the first screw slot 421*b*1 and the second screw slot 421*b*2 includes a plurality of slot positions. In addition, in FIG. 15, a plurality of slot positions of the first screw slot 421*b*1 and the second screw slot 421*b*2 are all connected to each other. In practice, the screw slot in the present disclosure may also include a plurality of separated hole positions, and the plurality of slot positions of the screw slot may also be slot positions respectively corresponding to the plurality of separated hole positions, which is not limited in the present disclosure.

Figure 16:
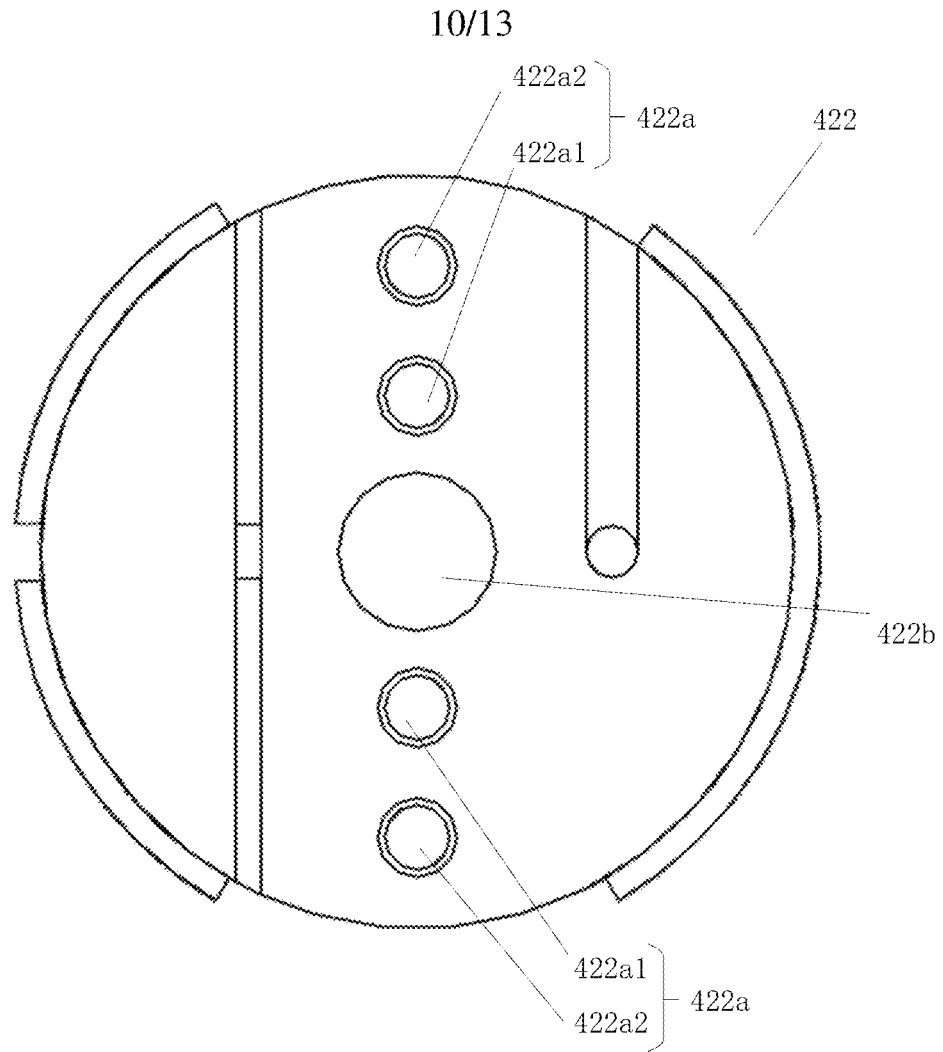
FIG. 16 is a schematic diagram illustrating a reel body according to an embodiment of the present disclosure.

As shown in FIG. 16, the reel body 422 in the embodiment of the present disclosure is provided with a fixed hole 422*a* and a reel central hole 422*b*. The fixed holes 422*a* may include a first fixed hole 422*al* and a second fixed hole 422*a*2. The reel central hole 422*b* may be a circular hole, and the reel central hole 422*b* may not exactly match the shape of the reel shaft 410. When the reel central hole 422*b* does not exactly match the shape of the reel shaft 410, the reel body 422 may rotate relative to the reel shaft 410.

Figure 17:
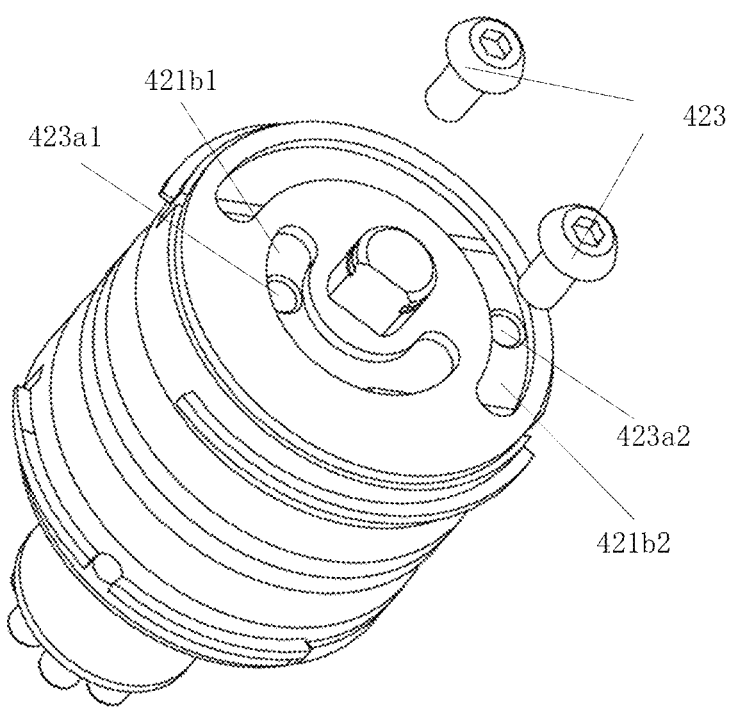
FIG. 17 is a schematic diagram illustrating a reel device according to an embodiment of the present disclosure.

In the embodiment of the present disclosure, the fixed hole 422*a* is configured to be fixed relative to one of the slot positions of the screw slot 421 by a screw 423. As shown in FIG. 17, the fixed hole 422*a* provided in the embodiment of the present disclosure includes a first fixed hole 422*al* and a second fixed hole 422*a*2. The first fixed hole 422*al* and one of the slot positions in the first screw slot 421*b*1 is relatively fixed by a screw 423, and the second fixed hole 422*a*2 and one of the slot positions in the second screw slot 421*b*2 are relatively fixed by the screw 423. When the reel shaft 410 rotates, the rotation of the transmission disc 421 is caused through the central through hole 421*a*, and the rotation of the reel body 422 is caused by the transmission disc 421, thereby moving the tight flexible push-pull wire wound on the reel body 422.

It should be noted that the reel body 422 is rotatable relative to the reel shaft 410, and the plurality of slot positions in the screw slot 421*b* are used for adjusting the angle between the reel body 422 and the transmission disc

421. Since the angle between the transmission disc 421 and the second reel 430 is fixed, in the present disclosure the relative angle between the first reel 420 and the second reel 430 can be adjusted by adjusting the angle between the reel body 422 and the transmission disc 421 to tighten the flexible push-pull wire.

In the embodiment of the present disclosure, the flexible push-pull wire in the push-pull drive assembly may be a steel wire. The flexible push-pull wire in the push-pull drive assembly is diverted via the sheath to connect to the reel device, and can also be diverted via the steering wheel to connect the reel device, which is not limited in the embodiment of the present disclosure.

Figure 18:
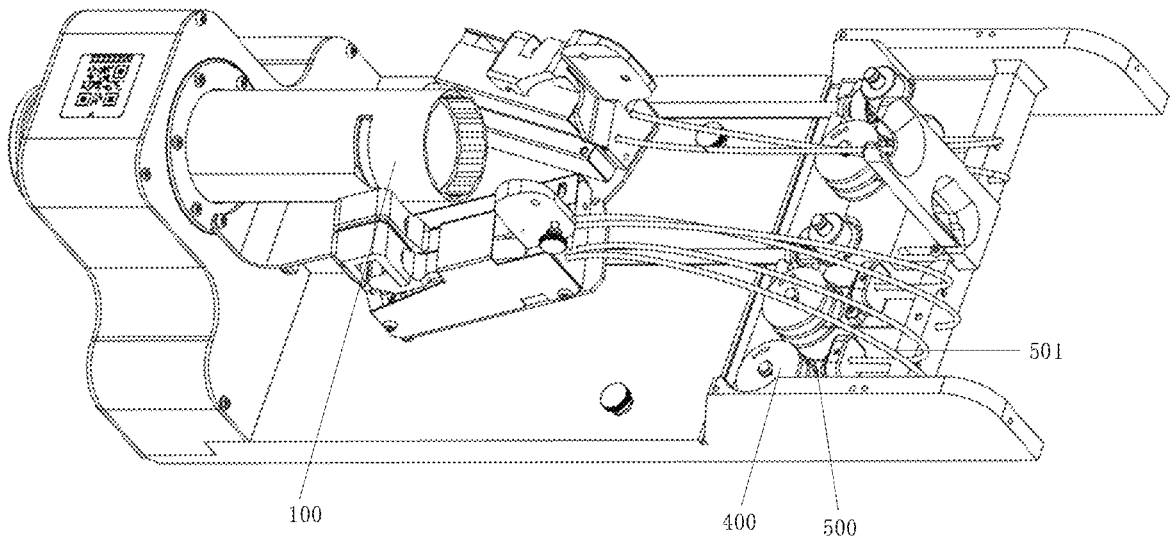
FIG. 18 is a schematic diagram illustrating a flexible push-pull wire diverted via a sheath according to an embodiment of the present disclosure.
Figure 19:
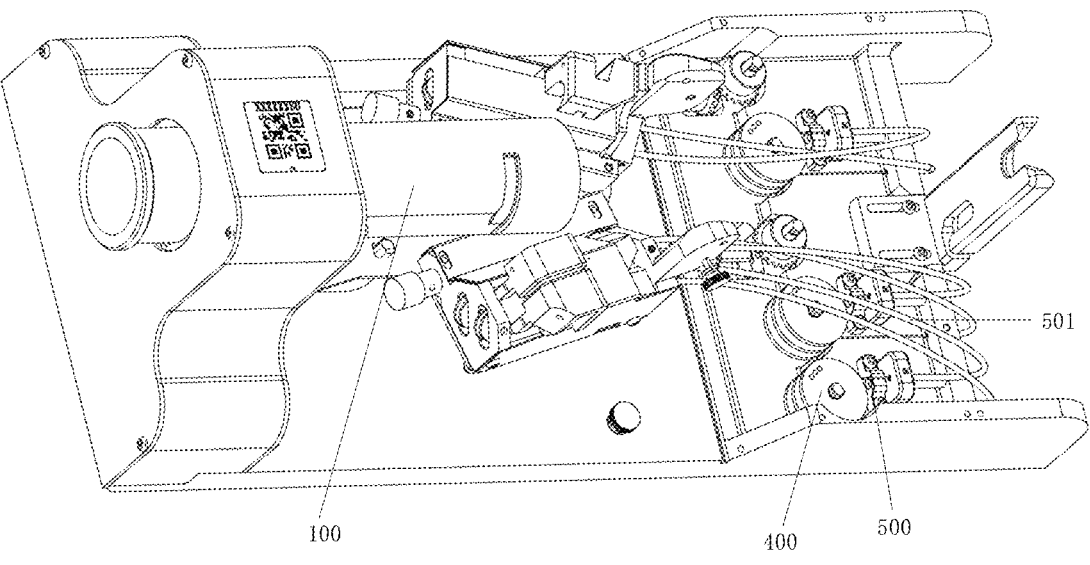
FIG. 19 is a schematic diagram illustrating a flexible push-pull wire diverted via a sheath according to an embodiment of the present disclosure.

As shown in FIGS. 18 and 19, the flexible push-pull wire 500 of the embodiment of the present disclosure may be diverted via a sheath 501 to connect to a reel device 400. A flexible push-pull wire extending from the instrument driving device 100 is provided inside the sheath 501 and is diverted along with the sheath 501 to connect to the reel device 400. In operation of the reel device 400, the flexible push-pull wire 500 moves within the sheath 501 to convert the action of the reel device 400 into a displacement action of the instrument driving device 100.

Figure 20:
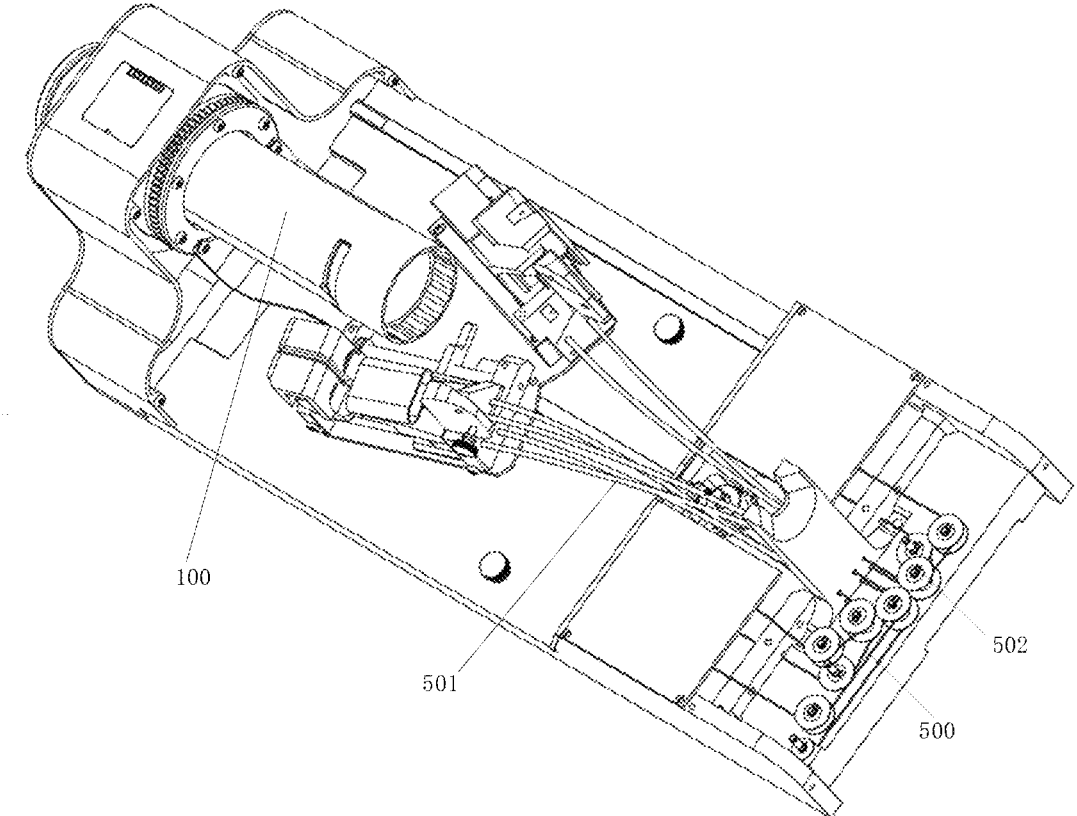
FIG. 20 is a schematic diagram illustrating a flexible push-pull wire diverted by a steering wheel according to an embodiment of the present disclosure.
Figure 21:
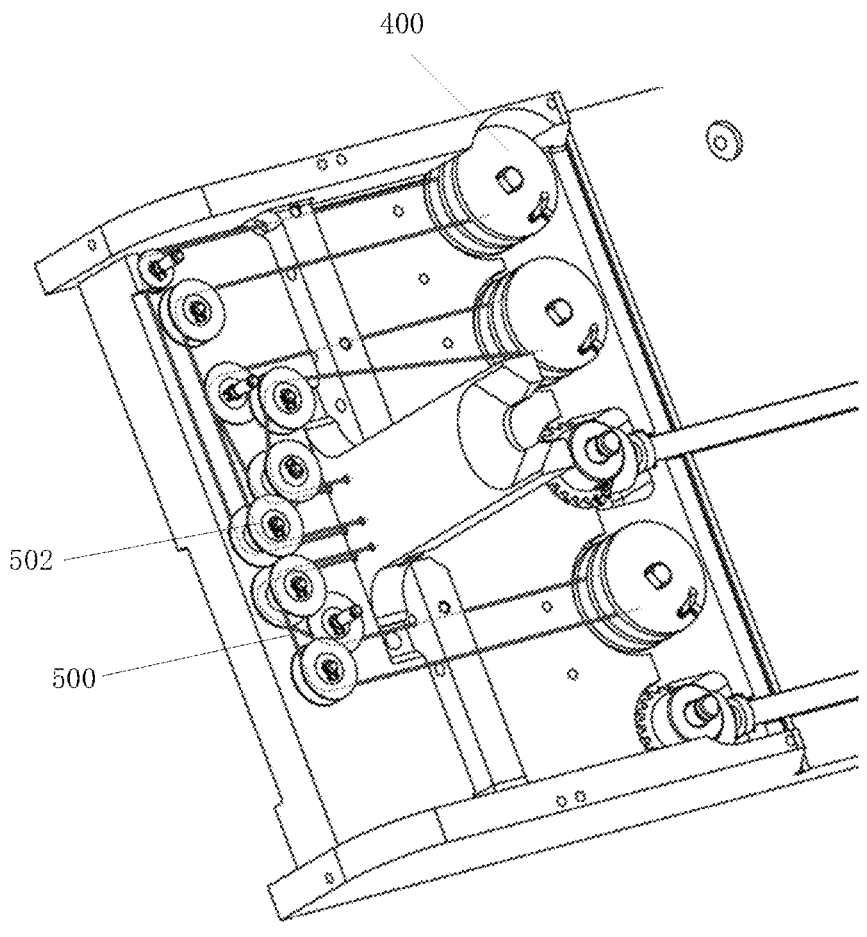
FIG. 21 is a schematic diagram illustrating a flexible push-pull wire diverted by a steering wheel according to an embodiment of the present disclosure.

As shown in FIGS. 20 and 21, the flexible push-pull wire 500 of the embodiment of the present disclosure can be diverted by the steering wheel 502 to connect to the reel device 400. The flexible push-pull wire 500 extending from the instrument driving device 100 in the embodiment of the present disclosure passes through the sheath 501, and is diverted by the steering wheel 502 and then connected to the reel device 400. It should be noted that the sheath 501 in the embodiment of the present disclosure is not provided with a steering structure, and the flexible push-pull wire 500 is diverted by the steering wheel 502 and is connected to the reel device. Therefore, when the reel device 400 is operated, the friction force of the flexible push-pull wire 500 moving inside the sheath 501 can be reduced, and the friction between the flexible push-pull wire 500 and the steering wheel 502 can also be reduced. Thus, the present embodiment can reduce the friction experienced by the flexible push-pull wire 500 during its movement, thereby increasing the service life of the flexible push-pull wire 500 and its associated components.

Figure 22:
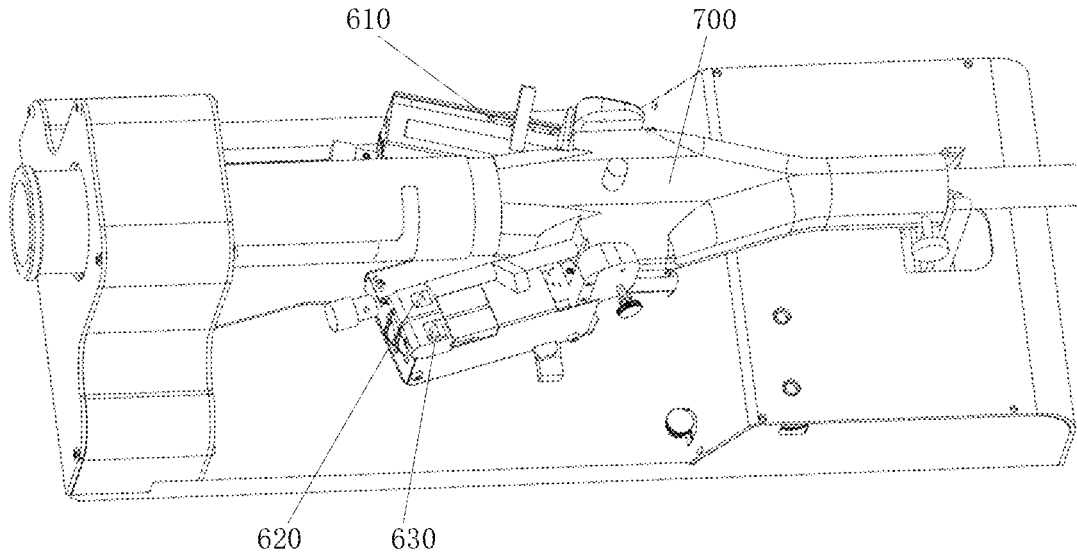
FIG. 22 is a schematic diagram illustrating an adapter according to an embodiment of the present disclosure.

In the embodiment of the present disclosure, the instrument driving device may be provided with a plurality of pins. As shown in FIG. 22, the embodiment of the present disclosure provides an instrument driving device that may include a first pin 610, a second pin 620, and a third pin 630. The plurality of pins in the embodiment of the present disclosure may be configured for adapting to a variety of surgical instruments 700. It should be noted that the surgical instrument can use one or more of the plurality of pins according to the requirements, which is not limited in the embodiment of the present disclosure.

The embodiment of the present disclosure also provides a surgical assistance device according to the adapter provided by the embodiments described above.

The embodiments of the present disclosure provide a surgical assistance system including a surgery performing device and the adapter in the above embodiment, where the surgery performing device is configured to drive the adapter.

It should be noted that the surgical assistance device of the embodiment of the present disclosure may include various components of the above embodiments of the adapter to achieve the same effects and functions, which will not be described in detail herein.

While illustrative embodiments of the present disclosure have been illustrated and described in detail in the drawings and foregoing description, they are to be considered as illustrative and not restrictive, it should be understood that only certain illustrative embodiments have been shown and described and that all changes and modifications that are desired to be protected within the spirit of the present disclosure as claimed are intended to be covered. It should be understood that although the words such as preferred, preferable, more preferable or most preferable are used in the above description to indicate that the described features may be more desirable, they may not be necessary and it can be conceived that embodiments without these features are within the scope of the present disclosure, which is defined by the appended claims. When reading the claims, the use of words such as "a," "an," "at least one," or "at least one portion" does not intend to limit the claims to only one, unless specifically stated otherwise in the claims. When using the language "at least a portion" and/or "a portion", the item may include a portion and/or the whole item, unless there is a specific contrary indication.

Although the spirit and principles of the present disclosure have been described with reference to several specific embodiments above, it should be understood that the present disclosure is not limited to the disclosed specific embodiments, and the division of various aspects does not mean that the features in these aspects cannot be combined. The present disclosure is intended to cover various modifications and equivalent arrangements within the spirit and scope of the appended claims.

What is claimed is:

1. An adapter comprising: an installation platform and an instrument driving device provided on the installation platform, the installation platform being installed on a surgery performing device; wherein the instrument driving device is in transmission connection with the surgery performing device and is configured to drive a surgical instrument;

the installation platform comprises a counting rack, a platform body and an installation bottom plate, wherein the platform body is in transmission connection with a power output shaft of the surgery performing device via the installation bottom plate, and the counting rack is installed on the platform body and configured to limit a number of usage times of the adapter; and a transmission shaft, wherein a first end of the transmission shaft is in transmission connection with the power output shaft, and a second end of the transmission shaft is in transmission connection with the instrument driving device, wherein the transmission shaft is provided with locking tabs, the counting rack is provided in a horizontal plane in a preset direction, a first row of teeth is provided on a side of the counting rack adjacent to the transmission shaft, and the preset direction comprises an axial direction of the transmission shaft; and the locking tabs are configured to extend into a groove of the first row of teeth and push an edge of the groove when the transmission shaft rotates, so that the counting rack is moved by a first distance in the preset direction.

2. The adapter according to claim 1, wherein the locking tab each comprises a ring body and a locking tab protrusion;

a ring width of the ring body in a radial direction is less than or equal to a distance between the transmission shaft and a tooth crest of the counting rack;

a length of the locking tab protrusion in the radial direction is greater than the distance between the transmission shaft and the tooth crest of the counting rack and less than or equal to a distance between the transmission shaft and the groove of the counting rack; and the locking tab protrusion is provided with a first ramp of a preset height in an axial direction, and when the transmission shaft rotates, the first ramp pushes the edge of the groove, so that the counting rack is moved by a first distance in the preset direction.

3. The adapter according to claim 2, wherein the installation bottom plate comprises a bottom plate protrusion and the platform body is provided with a second ramp;

the counting rack is provided with a second row of teeth at a side opposite to the first row of teeth, the first row of teeth and the second row of teeth are disposed alternately, and the second ramp is disposed below the second row of teeth;

the bottom plate protrusion is configured to lift the counting rack to separate the counting rack from the second ramp when the adapter is installed on the surgery performing device; and when the adapter is detached from the surgery performing device, the installation bottom plate is separated from the platform body, and an edge of one of the grooves of the second row of teeth of the counting rack slides down along the second ramp, so that the counting rack is moved by a second distance in the preset direction.

4. The adapter according to claim 3, wherein the platform body further comprises a compression spring having an upper end connected to the platform body and a lower end abutting against the counting rack; and when the adapter is detached from the surgery performing device, the installation bottom plate is separated from the platform body, the compression spring presses down the counting rack, and the edge of the groove of the second row of teeth of the counting rack slides down along the second ramp, so that the counting rack is moved by the second distance in the preset direction.

5. The adapter according to claim 3, wherein the counting rack is provided with a counting scale, the platform body is provided with a pointing mark, and the counting scale pointed by the pointing mark indicates a remaining number of usage times of the adapter;

the distance between every two counting scales is the sum of the first distance and the second distance.

6. The adapter according to claim 3, wherein when a remaining number of usage times of the adapter is 0, an end of the first row of teeth of the counting rack is stuck with the locking tab, so that the transmission shaft is non-rotatable.

7. The adapter according to claim 1, further comprising a push-pull drive assembly; and wherein the push-pull drive assembly comprises a reel device and a flexible push-pull wire provided between the instrument driving device and the reel device, and a reel shaft of the reel device is in transmission connection with the power output shaft of the surgery performing device.

8. The adapter according to claim 7, wherein the reel device comprises a first reel and a second reel that are coaxial;

one end of the flexible push-pull wire is connected to the second reel, and the other end of the flexible push-pull wire is connected to the first reel by passing through the instrument driving device; and the first reel and the second reel are configured to be twisted to tighten the flexible push-pull wire.

9. The adapter according to claim 8, wherein the first reel comprises a transmission disc and a reel body;

the reel shaft is a D-shaped reel shaft, and the transmission disc comprises a central through hole matching the shape of the reel shaft and a screw slot comprising a plurality of slot positions;

the reel body is provided with a fixed hole configured to be fixed relative to one of the slot positions of the screw slot via a screw; and the plurality of slot positions in the screw slot are configured for adjusting a relative angle between the reel body and the transmission disc to tighten the flexible push-pull wire.

10. The adapter according to claim 7, wherein the reel shaft of the reel device is in transmission connection with the power output shaft of the surgery performing device via a magnetic torque coupling.

11. The adapter according to claim 1, wherein the instrument driving device is provided with a plurality of pins configured for adapting to a variety of surgical instruments.

12. A surgical assistance system, comprising a surgery performing device and the adapter according to claim 1, wherein the surgery performing device is configured to drive the adapter.

\*     \*     \*     \*     \*